United States Patent [19]
Gebert et al.

[11] Patent Number: 6,063,402
[45] Date of Patent: May 16, 2000

[54] PURIFIED GALACTOMANNAN AS AN IMPROVED PHARMACEUTICAL EXCIPIENT

[75] Inventors: Mark S. Gebert, East Palo Alto; David R. Friend, Menlo Park; David Wong, San Francisco; Jagdish Parasrampuria, San Mateo, all of Calif.

[73] Assignee: Venture Lending, A Division of Cupertino National Bank, Palo Alto, Calif.

[21] Appl. No.: 08/487,605

[22] Filed: Jun. 7, 1995

[51] Int. Cl.⁷ .............................. A61K 9/20; C07M 1/00
[52] U.S. Cl. ......................... 424/464; 514/54; 514/169; 514/177; 514/782; 536/114; 536/124
[58] Field of Search ............................ 514/169, 54, 732, 514/177, 782; 536/114, 124; 424/464

[56] References Cited

U.S. PATENT DOCUMENTS 5,234,825  8/1993  McCeary et al. ..................... 435/101

OTHER PUBLICATIONS

Ikari, et al. "The Effect of Soluble Fiber Dietary Supplement on Constipation in 3 Patients with Dysphagia Who Suffered From Cerebral Infarction with Special Reference to Serum Diamine Oxidase Activity" *Jpn. J. Geriat* 1993, 30:402.

Chowdhury et al., (1988) "Single Step Purification of Polysaccharides Using Immoblilzed Jackfruit Lectin as Affinity Adsorbent" *Glycoconjugate* 5:27–34.

Noble et al., (1990) "Rheological Properties of Galactomannan–Based Gels. Part 1—Guar and Hydroxypropylguar Gels in Alkaline Media" *Carbohydrate Polymers* 12:203–217.

*Primary Examiner*—Elli Peselev
*Attorney, Agent, or Firm*—Cooley Godward LLP

[57] ABSTRACT

Disclosed is a substantially anhydrous, powdered, galactomannan composition consisting essentially of a galactomannan hydrocolloid exhibiting about 50% to about 90% by weight of anhydromannose residues and about 10% to about 50% by weight anhydrogalactose residues; less than about 1% by weight of protein material and less than about 3% of other nonaqueous impurities. This material is useful for preparing pharmaceutical compositions both in the substantially anhydrous form but preferably in an anhydrated form which includes about 5–15% by weight water. The pharmaceutical compositions comprise a therapeutically effective amount of a drug, the hydrated powered gallactomannan composition and optionally other pharmaceutically-acceptable excipients. When the hydrated powdered purified glactomannan of the invention is used to form a tablet, one sees improved hardness in the tablet formed. The pharmaceutical composition of the invention is particularly valuable for delivering a therapeutically effective drug to the colon without significant release of the drug in the upper GI tract after oral administration of the composition. Unique means to prepare the purified galactomannan in large quantities is provided.

8 Claims, 1 Drawing Sheet

Galactomannan Standard Curve Using Mannose and Galactose Sugars.

*FIG._1*

PURIFIED GALACTOMANNAN AS AN IMPROVED PHARMACEUTICAL EXCIPIENT

TECHNICAL FIELD

This invention relates to novel, highly purified galactomannan hydrocolloids and their use in pharmaceutical compositions.

BACKGROUND

Hydrocolloids that are available from higher plants have been known for years. Such hydrocolloids include, e.g., guar gum, locust bean gum (also referred to as carob gum), karaya gum, gum tragacanth and the like. These hydrocolloids, particularly guar gum, have found uses as food additives as thickeners, binders, stabilizers, moisture retainers, etc.; as dietary supplements for treating constipation; as pharmaceutical excipients to affect the binding, disintegrating or thickening characteristics of formulations of certain drugs; as flocculants, floatation agent, thickeners, binders, friction reducers, temporary plugging agents, etc., in the mining and oil well drilling industries.

Generally, these naturally occurring hydrocolloids are available in various levels of purity which may vary from source to source. The primary component of guar gum and locust bean gum is a galactomannan-based polysaccharide that consists of linear chains of (1→4) linked β-D-mannopyranosyl residues to which are attached (1→6) linked α-D-galactopyranocyl groups as single unit sidechains. The ratio of galactopyranose residues (generally given as anhydrogalactose to mannopyroanose residues (generally given as anhydromannose) varies from about 1:9 (about 10% by weight anhydrogalactose) to about 1:1.0 (about 50% by weight anhydrogalactose) depending on the source of the galactomannan. (See, e.g., Anderson, E. "Endosperm mucilagers of legumes: Occurrence and Composition," Ind. Eng. Chm. (1949) 41:2887–90.) Unfortunately, associated with the galactomannan-based polysaccharide are various impurities which can have an unpredictable and adverse affect on the composition as it is used in the pharmaceutical industry.

To obtain commercial grade galactomannan (e.g. guar gum from the guar seed), the hull (which is about 14–17% of the seed) is loosened by water soaking, then removed by multistage grinding and sifting, which takes advantage of the difference in hardness of the seed components. The germ, which is about 43–47% of the seed, is then removed by differential grinding using special types of hammer or roller mills. Finally, the remaining endosperm, which is about 35–45% of the seed and contains the galactomannan material, is ground to the desired particle size and marketed as food grade and pharmaceutical grade guar gum. Some of the remaining impurities include water (up to about 15% by weight), protein (up to about 10% by weight), acid insoluble matter (up to about 7% by weight), and ash (up to about 1.5%). Thus, up to 34% of the commercially available galactomannan-based polysaccharide compositions may be impurities.

It has been found that the commercially available guar gum generally does not provide a tablet with sufficient hardness ratings in higher concentrations to provide a tablet composition that will readily withstand the rigors of the tabletting process, storage and shipping. Thus, other excipients must be added to provide for the desired properties. Other excipients add additional bulk to the composition and make it more difficult to swallow as the tablet size increases.

It has been known that commercially available guar gum can be further purified by several methods. In one method, the gum is gently poured into water at about 60° C. under strong stirring for 1–2 hours to form a 2 gram/liter solution, then is centrifuged in a batch centrifuge to remove insolubles. The galactomannan is then precipitated by adding 2 volumes of 95° ethanol to 1 volume of the solution. The resulting precipitate is washed with ethanol, dried, crushed, dried under a vacuum and ground into a powder (see, O. Noble, et al., *Carbohydrate Polymers,* 12 (1990) 203–217). The resulting material was then placed in water to determine the Theological properties of the resulting gels and whether this might have implications for the oil well drilling industry. Another method for purifying guar is disclosed which uses a jacalin-sepharose 4B absorbent in an affinity chromatography technique (see S. Chowdhury, *Glycoconjuate J*. (1988) 5:27–34). This resulted in 4–12 mg quantities of polysaccharide that was quite pure and could then be further chemically characterized. No use was suggested and no properties were tested.

Surprisingly, it has now been found that by using highly purified galactomannan (such as guar gum) as a pharmaceutical excipient at high levels a drug-containing tablet can be prepared that shows a significantly higher hardness rating than a comparable tablet using standard, commercially available guar gum. It has also been found that such tablet composition, as well as capsule compositions, exhibit a significantly greater degree of cohesion over a longer period of time as compared to a tablet composition using standard, commercially available guar gum. The highly purified galactomannan also exhibits a significantly faster hydration rate, as well as a higher viscosity.

OBJECTS OF THE INVENTION

An object of this invention is to provide a stable purified, anhydrous galactomannan composition which is associated with less than 1% by weight of protein and less than 3% by weight of other impurities which is particularly valuable for forming pharmaceutical compositions.

Another object of this invention is to provide a hydrated, purified galactomannan composition that is valuable for preparing pharmaceutical compositions, particularly tablets that exhibit improved hardness characteristics.

Another object of this invention is to provide an improved pharmaceutical composition containing highly purified galactomannan.

Another object of this invention is to provide a process for preparing a purified galactomannan that is particularly valuable in preparing pharmaceutical compositions.

Another object of this invention is to provide a reliable method for the large scale preparation of highly purified galactomannan, particularly guar gum.

Another object of this invention is to provide a pharmaceutically acceptable tablet or capsule unit dosage form for oral administration that exhibits improved hardness and cohesiveness as compared to commercially available products.

Another object of this invention is to provide a pharmaceutical composition having a high percentage of purified galactomannan material and which shows an improved tablet hardness over the commercially available impure galactomannan such as guar gum.

SUMMARY OF THE INVENTION

One aspect of this invention is a substantially anhydrous, powdered galactomannan composition consisting essentially of a galactomannan hydrocolloid exhibiting about 50% to about 90% by weight anhydromannose residues and about 10% to about 50% by weight anhydrogalactose residues; less than about 1.0% in weight of protein material; and less than about 3.0% by weight other non-aqueous impurities.

Another aspect of this invention is a hydrated, powdered galactomannan composition consisting essentially of a galactomannan hydrocolloid exhibiting about 50% to about 90% by weight anhydromannose residues and about 10% to about 50% by weight anhydrogalactose residues; less than about 1.0% by weight of protein material; less than about 3.0% by weight other non-aqueous impurities; and about 5% to about 15.0% by weight water.

Another aspect of this invention is a pharmaceutical composition which comprises (a) a therapeutically effective amount of a drug;

(b) a hydrated, powdered galactomannan composition consisting essentially of (i) a galactomannan hydrocolloid exhibiting about 50% to about 90% by weight anhydromannose residues and about 10% to about 50% by weight anhydrogalactose residues; (ii) less than about 1.0% by weight of protein material; (iii) less than about 3.0% by weight other non-aqueous impurities; and (iv) about 5.0% to about 15% by weight water; and (c) optionally another pharmaceutically-acceptable excipient.

Still another aspect of this invention is a process for increasing the hardness rating of a pharmaceutical tablet that is to contain guar gum, which process comprises mixing a composition consisting essentially of a galactomannan-based hydrocolloid with a suitable active agent and a pharmaceutically acceptable excipient, and forming the pharmaceutical tablet by using a tablet press, wherein the purified galactomannan-based hydrocolloid exhibits about 50% to about 90% by weight anhydromannose residues and about 10% to about 50% by weight anhydrogalactose residues; less than about 1.0% by weight of protein material; less than about 3.0% by weight other non-aqueous impurities; and about 5% to about 15.0% by weight water.

Still another aspect of this invention is a pharmaceutical composition for preferentially delivering a therapeutically effective drug to the colon without significant release of the drug in the upper GI tract after oral administration of the composition, which composition comprises (a) about 0.5% to about 10.0% by weight of a drug that is useful for treating colon disorders or that is readily absorbed through the colon wall;

(b) about 80% to about 99% by weight of a purified galactomannan hydrocolloid; and (c) optionally up to about 20% by weight of another pharmaceutically-acceptable excipient.

DESCRIPTION OF SPECIFIC EMBODIMENTS

Compositions

This invention is based, at least in part, on the discovery that highly purified galactomannan has unique properties when used in pharmaceutical compositions. It has been found that by using highly purified galactomannan as a carrier for drugs a tablet having a significantly improved hardness rating can be obtained in compositions using a high percentage of the purified galactomannan as compared to commercially available galactomannan such as guar gum. In addition, pharmaceutical compositions having highly purified galactomannan as a base exhibit a higher level of cohesiveness over an extended period of time. This may be due to the significantly increased viscosity and higher rate of hydration, which can lead to a slower drug release from a composition due to the faster hydration and gel formation at the surface of the composition. On the other hand, loosely associated compositions using highly purified galactomannan tend to hydrate more readily and dissolve more quickly. While it has been known to purify, e.g., guar gum (See Noble, ibid), no attempt was made to remove nearly all of the water to form a stable anhydrous composition and use the material for pharmaceutical purposes. Similarly, the Chowdhury reference (ibid) provides a means for obtaining milligram quantities of material on a chromatography column, but suggest no use of the purified material.

One aspect of this invention is a substantially anhydrous powdered galactomannan composition consisting essentially of a galactomannan hydrocolloid exhibiting about 50% to about 90% by weight anhydromannose residues and about 10% to about 50% by weight anhydrogalactose residues. Alternatively, this may be stated that the galactomannan has a weight ratio of mannose to galactose of about 1:9 to about 1:1. This highly purified material is associated with less than about 1.0% by weight of protein material and less than about 3.0% by weight other non-aqueous impurities. Substantially anhydrous in this specification means less than about 1.0% by weight water.

The key ingredient of this invention is the polysaccharide hydrocolloid which is chemically designated as a galactomannan. Galactomannans are polysaccharides consisting of long chains of $(1\rightarrow 4)$-$\beta$-D-mannopyranosyl units to which single unit side chains of $\alpha$-D-galactopyranosyl are joined by $(1\rightarrow 6)$ linkages. Galactomannans are found in a variety of plants but differ in molecular size and the number of D-galactosyl side chains. The galactomannans useful in this invention are commonly found in the endosperms of the leguminosae. Examples of the family of legumes are set forth in Table 1 which shows the family and the percent endosperm content of leguminous seeds.

TABLE 1

Estimated Endosperm Content of Leguminous Seeds

| Family | Endosperm % |
|---|---|
| Acacia | 1–15 |
| Astragalos | 2–3 |
| Baryxylum | 30 |
| Caesalpinia | 8–40 |
| Cassia | 10–60 |
| Cercidium | 20 |
| Ceratonia (carob) | 50 |
| Chamaecrista | 8–15 |
| Colvillea | 30 |
| Crotalaria | 8–25 |
| Cyamopsis (guar) | 50 |
| Cytisus | 15 |
| Dalea | 20 |
| Daubentonia | 10–15 |
| Delonix | 25 |
| Desmanthus | 15 |
| Desmodium | 2 |
| Gleditsia | 30 |
| Glottidium | 2 |
| Glymnocladus | 15 |
| Indigofera | 20 |

TABLE 1-continued

Estimated Endosperm Content of Leguminous Seeds

| Family | Endosperm % |
| --- | --- |
| Lespedeza | 1–4 |
| Leucaena | 15 |
| Lotus | 2–4 |
| Lysiloma | 4 |
| Melilotus | 8–12 |
| Mimosa | 3–30 |
| Onomis | 25 |
| Parkinsonia | 25 |
| Parryella | 20 |
| Prosopis | 15 |
| Schrankia | 12 |
| Sesbania | 20 |
| Sophora | 20–25 |
| Trifolium | 3–10 |
| Virgilia | 20 |

Table 2 shows the approximate composition of some galactomannans from legume seeds and the percentage of anhydromannose residues versus the anhydrogalactose residues. As can be seen from Table 2, the percentage of anhydromannose may vary from about 50% to about 90% (e.g. 86%) of the composition of the galactomannan with the percent anhydrogalactose varying from about 10% (e.g. 14%) to about 50%.

TABLE 2

Proximate Composition of Some Galactomannans from Legume Seeds

| Name of Seed | Anhydro-mannose % | Anhydro-galactose % |
| --- | --- | --- |
| Caesalpinia spinosa (tara) | 71 | 26 |
| Caesalpinia cacalaco (huizache) | 69 | 28 |
| Ceratonia siliqua (carob, locust bean) | 80–86 | 20–14 |
| Cercidium torregyanum (palo verde) | 73 | 22 |
| Delonix regia (flame tree) | 79 | 19 |
| Cyamopsis tetragonolobus (guar) | 64 | 36 |
| Gleditsia triacanthos (honey locust) | 71 | 26 |
| Gymnocladus dioica (Kentucky coffee) | 71 | 26 |
| Sophora japonica | 81 | 16 |
| Desmanthus illinoensis (prairie-mimosa) | 70 | 26 |
| Indigofera hirsuta (indigo) | 72 | 23 |
| Cassia leptocarpa (senna) | 65 | 21 |
| Crotalaria intermedia (rattlebox) | 64 | 28 |
| Crotalaria juncea (rattlebox) | 60 | — |
| Crotalia striata (rattlebox) | 60 | — |
| Trigonella foenum graecum (fenugreek) | 52 | 48 |
| Medicago sativa (alfalfa) | 66 | 33 |

Preferably, the galactomannan that is most useful in this invention is derived from the *cyamopsis tetragonolobus*, commonly referred to as guar. This exhibits a percentage mannose residue of about 64% with a percent galactose residue of about 36%. The key to the composition of this invention is that the galactomannan-based composition is a highly purified and is associated with less than 1% protein material and less than 3% other non-water impurities. Preferably, the protein material is less than 0.5% and more preferably less than 0.3%, while the other non-aqueous impurities are preferably less than 2% and more preferably less than 1% by weight. Commercially available guar gum is about 70–82% galactomannan polysaccharide with protein, fat-extractable material, ash, moisture and other impurities making up the remainder of the composition. Sources of commercially available guar gum are Aqualon Company, Wilmington, Del.; Meer Corporation, Cincinnati, Ohio; Stein Hall & Company; and TIC Gums, Inc. The anhydrous, highly purified galactomannan is stable and can be used directly in preparing pharmaceutical compositions but may also be hydrated as discussed herein.

By using a hydrated, powdered highly purified galactomannan as a component of a drug-containing tablet or capsule, the need for large amounts of other excipients to provide necessary hardness characteristics can be minimized thus allowing for a smaller tablet. Thus, another aspect of this invention is hydrated, powdered galactomannan composition consisting essentially of about 85% to about 95% of a galactomannan hydrocolloid exhibiting about 50% to about 90% by weight anhydromannose residues and about 10% to about 50% by weight anhydrogalactose residues; less than about 1.0% by weight of protein material; less than about 3.0% by weight other non-aqueous impurities; and 5% to about 15.0% by weight water. Preferably, the powdered composition exhibits a particle size of less than 150 microns in diameter, with less than 125 microns being more preferred and less than 75 microns being most preferred.

This leads to another aspect of this invention, which is a pharmaceutical composition that comprises (a) a therapeutically effective amount of a drug; (b) highly purified powdered galactomannan composition, as described herein; and (c) optionally other pharmaceutically-acceptable recipients. Preferably the highly purified galactomannan is hydrated. It has been found, particularly in compositions that are tablets, the particle size of the powdered galactomannose is less than about 150 microns in diameter, more preferably less than 125 microns and most preferably less than 75 microns. Other preferences for the highly purified galactomannans also apply to the pharmaceutical compositions.

The compositions of this invention can accommodate a wide variety of drugs from highly active drugs that would be present at a level of about 1% or less (e.g. down to 0.1% by weight) in the composition to less active drugs that would be present at a level of about 60% by weight, or more (preferably about 5%–50% by weight). The highly purified galactomannan may be present in an amount from about 40% to about 99% by weight (preferably about 50%–90% by weight). While the need for other excipients is minimized by using the highly purified galactomannan, such additional excipients may be optionally added at levels that will help in the tabletting process (e.g. magnesium stearate as a lubricant), maintain stability of the drug (e.g. antioxidants), adjust the rate of disintegration (e.g. glucose), mask the taste (flavorings), increase hardness (HPMC), act as a binder (carbomers) or act as a coating. Generally no more than about 20% by weight of additional excipients will be needed, preferably less than about 10% and more preferably 5%).

The size of a unit dosage tablet or capsule of the composition of this invention will be less than about a gram, preferable less than about 750 milligrams, and even more preferably less than about 500 milligrams. However, if a powdered material is desired for mixing with water or juice to form a suspension up to 5 grams may be used, generally no more than about 2.5 grams.

A wide variety of drugs may be employed, where the subject compositions may find particular physiological advantage with particular types of drugs. The active ingredient, drug or therapeutic agent, can be any type of medication which acts systemically, which can be administered orally to transmit the active therapeutic agent into the gastrointestinal tract and into the bloodstream in therapeutically effective levels without early excessive peak concentrations, without being inactivated by physiological fluids, and without passing unchanged through the body of the patient or subject by being excreted unabsorbed. Thus, peptidic drugs are generally found not to be broadly suitable for use in the compositions of this invention for release into the upper GI. The type of drug that may be used in the compositions of this invention to advantage include the non-peptidic drug categories that exhibit a preferential window of absorption in the upper gastrointestinal tract and/or that are generally susceptible to sustained release. Individual drugs suitable for use in compositions of this invention are described in such publications as Goodman & Gilman's *Pharmaceutical Basis for Therapeutics*, (Goodman and Gilman) 8th edition (1990); *The Physician's Desk Reference* (1994-PDR); and Berger's *Medicinal Chemistry*. As such, these publications are incorporated herein by reference. Those drugs that exhibit a preferential window of absorption may be absorbed "passively" or "actively" in the upper gastrointestinal (GI) tract (i.e., the portion preceding the cecum and colon, i.e., the stomach, the duodenum and the jejunum). Examples of drugs of the passive absorption type include commercially available histamine $H_2$ receptor blockers such as ranitidine, cimetidine, famotidine, nizatidine, oxmetidine, and the like. Those drugs that exhibit a preferential window of absorption that are actively transported (generally referred to as a carrier-mediated membrane transport) are characterized by selectivity, competitive inhibition, congeners, a requirement for energy, saturability and movement against an electrochemical gradient. These include compounds such as angiotensin converting enzyme (ACE) inhibitors, β-lactam antibiotics and γ-aminobutyric acid (GABA)-like compounds. Representative ACE inhibitors are discussed in *Goodman and Gilman*, Eighth Edition at pp. 757–762, which is incorporated herein by reference. These include quinapril, ramipril, captopril, benzepril, fosinopril, lisinopril, enalapril, and the like and the respective pharmaceutically acceptable salts thereof. Beta-lactam antibiotics are those characterized generally by the presence of a beta-lactam ring in the structure of the antibiotic substance and are discussed in Goodman and Gilman, Eighth Edition at pp. 1065 to 1097, which is incorporated herein by reference. These include penicillin and its derivatives such as amoxiciffin and cephalosporins. GABA-like compounds may also be found in Goodman and Gilman. Those compounds that lend themselves well to sustained release include calcium channel blockers (such as nifedipine, nicardipine and diltiazem); appetite suppressants, such as phenylpropanolamine hydrochloride; stimulants, such as caffeine; water soluble and fat soluble vitamins or precursors, such as vitamin C, vitamin B-12, tocopherol, vitamin D, vitamin A, β-carotene, etc.; antihypercholesterolemics, such as Gemfibrozil and lovastatin; antitussives, such as dextromethorphan and its hydrobromide, noscapine, carbetapentane citrate, and chlophedianol hydrochloride; antihistamines, such as chlorpheniramine maleate, phenidamine tartrate, pyrilamine maleate, doxylamine succinate, and phenyltoloxamine citrate; decongestants, such as phenylephrine hydrochloride, phenylpropanolamine hydrochloride, pseudoephedrine hydrochloride, ephedrine; β-adrenergic receptor antagonists (such as propranolol, nadalol, timolol, pindolol, labetalol, metoprolol, atenolol, esniolol, and acebutolol). Using such compounds, the compositions of this invention are adjusted to achieve increased gastric residence time, increased mean residence time in the upper GI and sustained release.

While the highly purified galactomannan compositions of this invention exhibits the improved characteristics known to the commercially available galactomannan compositions such as guar gum, namely a cytoprotection or mucosal protections, or as discussed in U.S. Ser. No. 08/347,601. Thus, the pharmaceutical composition of this invention may include NSAID as a drug useful in this invention. A wide variety of NSAIDs may be employed, but the subject formulations find particular physiological advantage with aspirin. Individual NSAIDs suitable for use in compositions described in such publications as Goodman & Gilman's *Pharmaceutical Basis for Therapeutics*, (Goadman and Gilman) 8th edition (1990), Chap. 26; *The Physician's Desk Reference* (1994-PDR); and Berger's *Medicinal Chemistry*. As such, these publications are incorporated herein by reference. Representative NSAIDs and families of NSAIDs useful in the compositions of this invention include the salicylates, pyrazolons, indomethacin, sulindac, the fenamates, tolmetin, propionic acid derivatives, and the like. Specific compounds include salicylic acid, aspirin, methysalicylate, diflunisal, salsalate, phenylbutazone, oxyphenbutazone, apazone, mefenamic acid, meclofenamate sodium, ibuprofen, naproxen, naproxen sodium, fenoprofen, ketoprofen, flurbiprofen, piroxicam, diclofenac, etodolac, nabumetone, and the like. Aspirin is preferred. Alternatively the compositions of this invention may be modified to preferentially deliver drugs to the colon by not releasing significant amounts to the upper GI tract. Thus, this invention provides a vehicle for delivering drugs preferentially to the colon, i.e., 50% or more of the drug will be released in the colon. Among the drugs for which this will be useful are drugs for the treatment of chronic diseases of the colon, including inflammatory diseases. These drugs may include certain glucocorticoids, stimulant laxatives, peptides, antibodies, anticholenergics, and other drugs such as diphenoxylate, loperamide, codeine, metronidazole, 5-amino salicylic acid (5-ASA), sulfasalazine. Of these compounds, particularly valuable and therefore preferred are the glucocorticoids (also known as corticosteroids) for treatment of IBD. These include hydrocortisone (and pharmaceutically-acceptable salts or esters such as the acetate, cypionate, sodium phosphate, sodium succinate, butyrate, valerate, etc.), beclamethasone, beclamethasone dipropionate, betamethasone (and its pharmaceutically-acceptable salts or esters such as the benzoate, dipropionate, sodium phosphate, acetate, valerate, etc.) cortisone, cortisone acetate, dexamethasone, dexamethasone acetate, dexamethasone sodium phosphate, flunisolide, methylprednisone, methylprednisone acetate, methylprednisone sodium succinate, paramethasone acetate, prednisilone, prednisilone acetate, prednisilone sodium phosphate, prednisilone tebutate, prednisone, triamcinolone, triamcinolone acetinide, triamcinilone diacetate, triacsinilone hexacetonide, alclometasone dipropioante, amcinonide, clobetasol propionate, clocortilone pivalate, desonide, desoximetasone, diflorasone diacetate, fluocinolone acetonide, fluocinonide, fluorometholone, flurandrenolide, halcinonide, medrysone, mometasone furoate, budesonide, fluticasone, and the like. Other steroids may be apparent to one of ordinary skill in the art. The chemical names of these can be found at page 1451 of Goodman and Gillman's "The Pharmacological Basis of Therapeutics," 8th edition or in the Eleventh Edition of the Merck Index. Of these, dexamethasone, budesonide and fluticasone are preferred. Other drugs that are useful in this invention include ACE inhibitors such as captopril, stimulant laxatives (for example, docusate sodium, senna concentrates [sennosides], bisacodyl, potassium bitartrate, and the like), and peptides such as LHRH or its derivatives (e.g., leurprolide acetate, nafarelin, gosarelin, and the like). The amount of the active drug that will be included in the composition will vary depending upon the activity of the drug relative to the condition being treated. In general, there will be no more than about 20% of the active compound in the composition with a minimum amount of about 0.1% by weight. Preferably, the amount will vary between about 1% to about 4% by weight.

Process of Preparation

Generally, the commercially available galactomannan, which may contain only about 66% by weight pure galactomannan, can be purified by means known in the art. For example, see the Noble, et al. article mentioned herein for a batch centrifugation process and the Chowdhury article, also mentioned herein, for an affinity chromatography technique. Unfortunately, each of these methods provides very limited quantities of material and provided no suggestion that it could be used for pharmaceutical purposes. A process has now been found to make large quantities of highly purified galactomannan from commercially available material. By taking certain precautions purified material can be prepared on a relatively large scale basis by separating the aqueous galactomannan solution from insolubles then precipitating solid galactomannan form solution and recovering.

One method for preparing large scale amounts of purified galactomannan material is the use of a continuous centrifuge that is capable of obtaining a rotational speed in revolutions per minute (rpm) at least about 12,000 and preferably about 20,000 to provide a centrigue G force of about 8500 Gs (cm/sec). In using the continuous centrifuge, a solution of commercially available guar gum is passed through the centrifuge to give a supernatant that is clear and has greatly reduced protein material. A water-miscible, pharmaceutically acceptable solvent, in which the galactomannan is insoluble, is mixed with the supernatant to precipitate the galactomannan which is then collected, dried and ground to give purified galactomannan. Certain parameters of the process are important to ensure that the highest quality galactomannan is obtained. In the first step of obtaining a suitable solution one needs to ensure that there is a good solid separation that will occur in the centrifuge to separate the dissolved galactomannan material from the associated proteinaceous material or other insoluble material which accompanies the commercially available material. Generally the concentration of the aqueous mixture will be less than about 1% weight/volume (w/v) of the galactomannan, but preferably will be no more than concentration of 0.5% w/v. While this concentration may vary depending on the source of the crude galactomannan, less than 0.5 w/v will generally be used. As a lesser concentration is used a greater volume will be needed to obtain a similar quality of the purified galactomannan. In preparing the solution the commercially available guar gum for example is dissolved very slowly by adding small quantities of the material to water being rapidly stirred at a temperature of about 0–60° C. Preferably the addition is simply done at room temperature under conditions that avoid clumping of the material and increasing the amount of time for the material to then dissolve. Once the material has been added to the water agitation is continued for up to 10 hours but generally no more than about 3 hours (less than 2) will be required for a complete dissolution to provide a clear aqueous mixture.

The separation of the galactomannan solution may be carried out with any suitable centrifuge that provides the appropriate G rating or a high pressure filtration system. In general the separation can be carried out at a temperature of between 0–60° C. preferably will be carried out at room temperature. The A suitable continuous centrifuge is a Sharples model T1P continuous centrifuge. This model can run up to 50,000 revolutions per minute. Preferably the rotational speed for the Sharples is run at least 12,000 revolutions per minute and preferably more than 20,000 revolutions per minute. In general the operating speed that is found to work best is 50,000 RPMs but that rate can be adjusted to match the flow rate of the solution through the centrifuge. In general the flow rate and liters per hour for that centrifuge at 50,000 RPM will be less than about 5 liters per hour but anything less than that amount should provide a centrifuge effluent with a clarity that is very good indicating that the suspended proteinaceous material has been centrifuged out. Thus the flow rate may be from about 1 liter per hour to about 5 liters per hour preferably less than about 4.2 liters per hour. It will be apparent to one of ordinary skill in the art that to maximize the throughput while ensuring that you have a high clarity of the resulting effluent the sample concentration should be as high as possible with the flow rate as high as possible while still giving good separation of the undissolved solids and excellent clarity of the supernatant layer. In general if the RPMs are at 50,000, the sample concentration of 0.4% w/v with a flow rate of 4.2 liters per hour results in an excellent product. It has been found that because of the quantities of air used to drive the centrifuge if there are impurities the clarity of the resulting effluent and the purity in the appearance of the ultimately obtained purified guar can be adversely affected. It is part of this invention that purified air must be used to drive the centrifuge. Such purification can be readily obtained by using filters of approximately 0.01 microns to ensure that any pollutants or air particles are not included in the air that is being used for the centrifuge.

Alternatively a large batch centrifuge may be used as well. Also the aqueous solution of the commercially available material may be filtered under pressure. A suitable plate and frame filter press is discussed in Remington's Pharmaceutical Sciences, 18th Edition at pp. 1465–66. In operation of such a high pressure filter, material to be filtered enters the apparatus under pressure through a pipe at the bottom and is forced into one of the many chambers. A filter cloth is positioned on both sides of each chamber. As the material passes through the filtering cloth, solids remain behind in the chamber and the clear filtrate passes through and out of an opening located on top of the apparatus.

The next step in the process involves the precipitation of the purified galactomannan by slowly mixing the resulting centrifuge effluent with an appropriate volume of a water-miscible, pharmaceutically-acceptable solvent which causes the precipitation to take place. Such a solvent may be an appropriate solvent in which the galactomannan is insoluble. Any of the process pharmaceutical acceptable lower alkyl alcohols or ketones are suitable, such as ethanol, isopropyl alcohol, acetone, and the like. Ethanol is preferred. While the ratio of the volumes of the water-miscible solvent to the centrifuge effluent may vary from about 1 to to 5 to 1, it is preferable to use approximately equal volumes of material and to minimize the amount of the water-miscible solvent and thus minimize the amount of recovery that one needs to do in the precipitation process. To minimize the volume of solvent used, the volume of the aqueous effluent may be reduced by evaporating water before adding the solvent. In general the precipitation can take place at any temperature between 0–60° C. Preferably it is carried out at room temperature. Once the precipitation occurs the resulting mixture is continued to be agitated and the resulting solids are separated from the liquids by any means known such as centrifuging or filtering. It is found that filtering through a stainless steel wire mesh screen and compressing to squeeze out any excess fluid is suitable. The screen mesh size is any size that is suitable for retaining the material on it.

Once the precipitated material is separated from the liquid it is dried until the water content is below about 1%. The resulting material will be a solid having a color varying from snow white to very pale yellow or yellow green depending on the origin of the galactomannan and its purity from the commercial source. Preferably the resulting purified galactomannan is dried under a vacuum at less than 100° C. preferably at 70° C. or less for a period of time sufficient to dry the material. Generally this is found to be less than 10 hours with 8 hours being sufficient.

Once the dried material is obtained it is further broken up by any means known in the art to provide a suitable particle size. The larger pieces on the smaller scale can be simply broken up by hand using a hammer then ground in a suitable mill or grinder passing through an appropriate sieve to give the appropriate particle size. In general any of the means of producing powders may be used in the milling of the material. Thus intermediate and fine grinding mills that work through attrition, rolling or impact may be used in reducing the particle size. Thus, roller mills, hammer mills centrifugal impact mills, cutter mills, attrition mills and other types of equipment may be used to reduce the particle size. A further discussion of the kinds of milling that can be done is found in Chapter 88 of Remington's Pharmaceutical Sciences, 18th edition, Mac Publishing Company, pp. 1615–1632, which is incorporated herein by reference.

It has been found that the particle size has an impact on the degree of hardness resulting from the material which is produced in accordance with this invention. It is preferred to produce particles that have a particle size of about 150 microns or less to provide the greatest increase in the hardness rating for the tablets of this invention. Preferably this will be less than 150 microns down to 125 microns in size and even more preferably less than 75 microns in size. Thus a sieve number 100 would give a micron size of about 150 with a number 120 sieve giving a micron size of 125 and a number 200 sieve giving a micron size of 75 or less.

Preferably the material is then rehydrated to a level of less than about 15% by weight but generally more than about 5% by weight by allowing the material to rehydrate in a humidity chamber at a relative humidity between about 50–90 relative humidity.

In preparing the pharmaceutical compositions of this invention particles of the drug are combined with the powdered, highly purified glactomannan and other excipients using standard powder mixing and blending techniques. Such techniques are discussed, for example, in Chapters 88 and 89 of Remington's Pharmaceutical Sciences, 18th Edition, Mack Publishing Company and is incorporated herein by reference. Representative equipment includes rotating-shell mixers (e.g. a cross-flow blender), fixed shell mixers, Muller mixers, vertical impeller mixers, motionless mixers and the like. The resulting mixture is then prepared as a unit dosage, e.g., as a tablet or, preferably, as a capsule in accordance with known techniques such as those set forth in *Remington's* (Eighteenth Edition) in Chapter 89.

Other excipients are then mixed with the galactomannan and drug. These excipients may belong to the category known in pharmaceutical arts as binders and fillers. These tend to aggregate particles, and are often employed in tabletting to reduce friability and improve hardness. Strong binders in general will be employed in small proportions, usually less than 5%, frequently than 0.5% of the weight of the dosage form, if used at all. An exemplary group of strong binders are carboxypolymethylene, referred to as CARBOPOL and CARBOMER, or cross-linked polymers of acrylic acid. In large amounts, they interfere with disintegration of the dosage forms, and should be used in small proportions or avoided altogether for compositions for the upper GI. Larger quantities can be used for colonic delivery.

Non-gas-forming filler materials may be used and are typically inert substances for dispersing a drug within the particle mass while being conducive to slow hydration of the mass during migration through the gastrointestinal tract. Preferably, the filler material includes a hydrophilic sol-forming polymer for modulating the hydration characteristics of the particle mass. Exemplary sol-forming polymers include polyvinylpyrolidone (PVP), polyacrylic acid cross-linked with divinyl glycol (polycarbophil), and the like.

Other excipients are mineral salts. Preferred mineral salts dissolve in gastric juice, thereby aiding in the disintegration of the dosage form and hydration of the hydrocolloids in the upper GI tract. These may include minerals salts such as alkaline earth (e.g., $Ca^{+2}$, $Mg^{+2}$) phosphates and sulfates.

Other excipients may include fatty acids, phospholipids, and fatty acid salts (e.g., magnesium stearate) and waxes. These components may impart lubricating properties to the composition. Other lubricants include MYVATEX® and SYLOID® brand lubricants. Other excipients may include synthetic emulsifiers (e.g., sodium lauryl sulfate) and surfactants, such as polyakylene glycols (e.g., polyethylene glycol-PEG) and Eudragits.

In one embodiment, the composition is contained in a capsule, such as a gelatin capsule available from Elanco Qualicaps (Indianapolis, Ind.) or Capsugel (Warner Lambert, Morris Plans, N.J.). Other suitable capsules include soft elastic capsules.

Alternatively, the particle mass can be coated with a coating, e.g., lactose, or with a polymer coating such as Eudragits (Rohm Pharma, Darmstadt, Germany) or various cellulose derivatives.

Tablets are prepared in accordance with methods known in the art such as those set forth in Chapter 89 in Remington's.

It is contemplated that the galactomannans of this invention may be used for other pharmaceutical compositions such as those set forth in U.S. Pat. Nos. 5,096,714; 5,118,510; and 5,292,518. All of those patent are incorporated herein by reference.

EXAMPLE 1

This example sets forth a method of preparing a pure galactomannan which is useful in the composition of this invention and shows the difference in characteristics of a composition of this invention as compared to a composition using the commercially available galactomannan. Commercially available guar gum was purchased from Aqualon, Inc. as G3-NF, Lot No. A3335D. A solution of guar gum was prepared as a 0.2% solution in water by allowing it to dissolve overnight with stirring at room temperature. The resulting solution was then centrifuged at 3000 RPMs for 10 minutes to remove the insoluble material, and the clear remaining solution was precipitated using an equal volume of 95% ethanol, forming a fibrous, white, gel-like precipitation and leaving behind a pale yellow solution. The white solid was dried and ground to approximate particle size of 200 micron using a Krupps coffee mill to form a fine white powder. The yield of purified galactomannan was 70%. Viscosity and hydration rates were measured on a Brookfield Viscometer using a spindle No. 3 at 20 RPMs and a solution concentration of 1% w/v. Differential scanning calorimetry (DSC) was performed using a Dupont 2100 DSC at 10° per minute heating rate. The following table summarizes the physical/chemical differences between commercially available guar gum and the purified material. Note particularly the unusual differences in hardness.

| Observable | Unpurified | Purified |
|---|---|---|
| Color | Pale Yellow | White |
| Particle Size ($\mu$) | Small~100 | Large~200+ |
| Protein (%) | 4.00 | 0.94 |
| Tablet Hardness (Kp) | 0.00 | 3.60 |
| Hydration Rate (cp/log hrs) | 2,078 | 5,233 |
| Maximum Viscosity (cp) | 3,500 | 5,000 |
| Moisture Sorption at 95% RH (%) | 42.70 | 55.20 |

EXAMPLE 2

In addition to the physical chemical studies summarized in the above Table 3, two dissolution studies were run preparing capsules of purified and unpurified guar with raniditine HCl (2:1 portion of guar gum to raniditine). Capsules containing a composition of this invention were prepared and were compared to similarly prepared capsules containing a composition using commercially available guar gum. The first study involved dissolution with stirring at 20 RPMs in distilled water. The purified guar gum capsule hydrated more rapidly and stayed together as a gelatinous mass while the unpurified version quickly started to disintegrate forming a slightly turbulent solution. After 18 hours, the unpurified capsule was lifted out of the solution and fell apart in less than 2 minutes. The capsule with purified material was lifted out and did not fall apart even after 20 minutes. The purified capsule had formed a rigid material which fell apart only after significant mechanical agitation.

The gel integrity of the capsule containing a composition of this invention was further illustrated by performing a similar dissolution study at 200 RPM. In this study, the encapsulated, unpurified composition disintegrated within several minutes, while the purified capsule quickly formed a rigid gel-like mass which resisted disintegration after even about 2 hours of agitation. These studies establish the significant improvement in the pharmaceutical composition employs the purified guar as compared to the unpurified material.

EXAMPLE 3

This example shows a process of this invention for preparing larger quantities of highly purified galactomannan from different sources of commercially available guar gum obtainable from the manufacturers indicated below. Using the process of this invention, namely a continuous centrifuge, larger quantities of pure guar gum are available than was previously possible to obtain. Commercially available samples of guar gum were obtained as follows:

1. Aqualon Corporation G3-NF Lot No. A1342 FR.
2. Meer Corporation MMM1/2 Lot. No. 02-0142.
3. TIC Gum Corp. TIC8/22A Lot No. S21602.
4. TIC Gum Corp. SCM Lot No. B21452.
5. Aqualon Corporation G3-NF Lot No. A3335D.

The following operating parameters for purification of the commercially available material are as follows:

A. Dissolution

The guar gum is dissolved very slowly by sprinkling the powder into the vortex of the rapidly stirred beaker of distilled water at room temperature. The powder is carefully added slowly to avoid clumping of the guar gum. Clumping will result in a much slower procedure of the dissolution and hydration of the material. Sufficient guar gum is added to provide a final concentration of guar gum in water of 0.4% by weight. Once the guar has been added to the solution, the solution is stirred for approximately three hours.

B. Centrifugation

Centrifugation was performed at room temperature with a Sharples models T1P continuous centrifuge running at fifty thousand revolutions per minute. The flow rate of the 0.4% guar solution through the centrifuge was 4 liters per hour. The air used to drive the centrifuge was purified of oil, water and dirt by passing it through filters of approximately 0.01 micron. This is important to ensure that the air has no particles that will discolor the material.

C. Precipitation

Once a solution of purified guar was obtained from the centrifugation step, the solution is slowly poured into an equal volume of 95% ethanol while it is stirred rapidly. A mass of white galactomannan polymer rapidly forms and the precipitate is separated from the pale yellow water mixture by filtering through stainless steel wire mesh screen and pressing into a flat pancake to squeeze out any excess ethanol and water.

D. Drying

The resulting precipitated guar gum is dried under a vacuum at 70° C. for eight hours or until the guar is dry. The resulting solid will vary from pure white to a very pale yellow or yellow green material.

E. Milling

Figure 1:
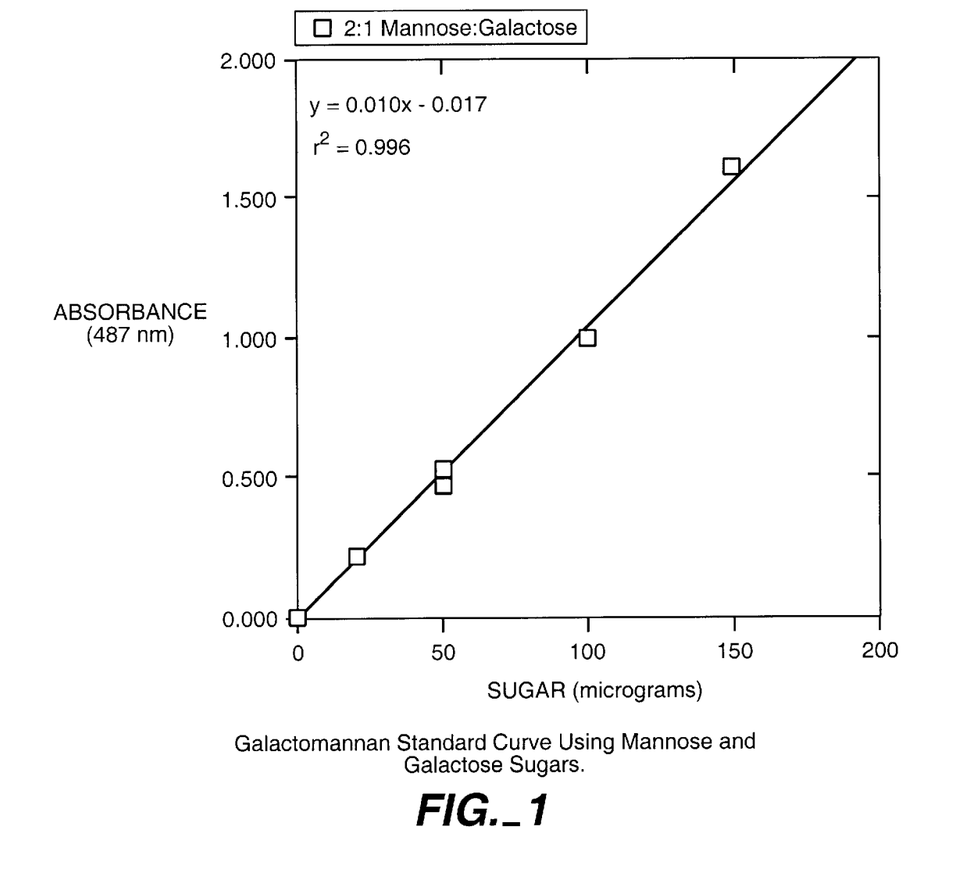
FIG. 1 shows a galactomannan standard curve using mannose and galactose sugars.

Samples are first broken up into approximately one inch diameter pieces by hand with a small hammer. These pieces are then ground in a crux coffee mill for thirty seconds to a minute, then passed through a 215 micron sieve. Samples are kept in open containers to allow them to equilibrate with the room humidity. The samples of the commercially available material and the purified material were characterized for chemical composition in terms of protein, galactomannan and acid and soluble matter. The protein content is determined by measuring the nitrogen content of the sample val elemental analysis and multiplying by 6.25 as outlined in the USP IINF XVII Method 1 under nitrogen determination. Acid soluble matter is determined by dissolving the sample in sulfuric acid and weighing the remaining solvent as outlined in the USP under guar gum. Galactomannan content was determined by an assay based on a paper entitled "Colometric Method for Determination of Sugars and Related Substances" by DuBois, M., Gilles, K A., Hamilton, J. K., Reebers, P. A., and Smith, F. Analytical Chemistry, 1956, 28, 3, 350–355. Since the galactomannan component of guar consists of polysaccharide with a manosticolactos ratio of about two to one, a sugar solution containing this ratio of manosticolactose was used as a galactomanos standard. Two mls of sugar per guar are added to a small test tube to give a total mass material between 10 and 150 micrograms. Fifty microliters of an 80 weight percent phenol-water solution was added to the test tube followed by 5 milliliters of concentrated sulfuric acid resulting in the formation of a pale yellow solution. The absorbance of this solution is measured at 487 NM and subtracted from a blank solution containing only distilled water phenol and sulfuric acid. The absorbance at 487 NM versus sugar quantity added for the sugar standard used is shown in FIG. 1, can be seen from this figure that the sugar standard exhibits a linear absorbance curve up to 150 micrograms of sugar. To assay the guar gum, a solution of guar containing 50 micrograms of guar per mil a liter of water is prepared. Water and soluble components are removed by centrifuging the solution to milliliters of the resulting supernatant is added to a small test tube followed by phenol and sulfuric acid, the absorbance at 487 is measured and the quantity of galactomannan is determined from FIG. 1. This quantity is divided by the total quantity of guar gum used to obtain the fraction of water soluble galactomannan present in the guar sample. The results of the galactomannan assay are shown in Table 2 for the various guar samples used in the process of this invention in this example.

TABLE 3

| Sample No. | Sample Wght. (ug) | Absorbance (487) nm) | Soluble Galactomannan Wght. (ug) | Percent Galactomannan | Normalized Percent Galactomannan |
| --- | --- | --- | --- | --- | --- |
| 1 | 101.30 | 0.719 | 73.60 | 72.66 | 66.05 |
| 1-P | 101.20 | 1.005 | 102.20 | 100.99 | 91.81 |
| 2 | 102.30 | 0.723 | 74.00 | 72.34 | 65.76 |
| 2-P | 101.40 | 1.022 | 103.90 | 102.47 | 93.15 |
| 3 | 101.50 | 0.681 | 69.80 | 68.77 | 62.52 |
| 3-P | 100.70 | 1.086 | 110.30 | 109.53 | 99.58 |
| 4 | 104.20 | 0.680 | 69.70 | 66.89 | 60.81 |
| 4-P | 104.10 | 1.086 | 110.30 | 105.96 | 96.32 |
| 5 | 103.00 | 0.746 | 76.30 | 74.08 | 67.34 |
| 5-P | 100.00 | 1.013 | 103.00 | 103.00 | 93.64 |

"1-P, etc., refers to a purified guar from source 1, while "1", etc., refers to the commercial guar with impurities. It can be seen that when the percent soluble galactomannan as calculated directly from the manos-galactose sugar standard, this slightly over estimates the galactomannan content. To correct for this the galactomannan percent has been normalized by the highest galactomannan percent found. A summary of all the chemical composition of guar gum is shown in Table 3.

TABLE 4

| Guar Gum # | Galactomannan | Protein | Acid Insolubles |
| --- | --- | --- | --- |
| 1 | | | |
| Raw Material | 66.01$^i$ | 3.31 | 2.71 |
| Purified Galactomman | 91.81$^i$ | 0.25 | 2.37 |
| Protein Rich Impurities | 85.45$^{ii}$ (22.72$^i$) | 10.81 | N/D$^{ii}$ |
| 2 | | | |
| Raw Material | 65.76$^i$ | 4.25 | 4.61 |
| Purified Galactomannan | 91.81$^i$ | 0.06 | 1.13 |
| Protein Rich Impurities | 78.18$^{ii}$ (26.36$^i$) | 8.06 | N/D |
| 3 | | | |
| Raw Material | 62.52$^i$ | 3.94 | N/D |
| Purified Galactomannan | 99.57 | 0.00 | N/D |
| 4 | | | |
| Raw Material | 60.81$^i$ | 2.50 | N/D |
| Purified Galactomannan | 96.32 | 0.00 | N/D |
| 5 | | | |
| Raw Material | 67.34$^i$ | 2.88 | 1.47 |
| Purified Galactomannan | 93.64 | 0.00 | 1.74 |
| 2 | | | |
| Raw Material 250–180$\mu$ | 65.01$^i$ | 4.19 | N/D |
| Raw Material 125–106$\mu$ | 66.47$^i$ | 4.13 | N/D |
| Raw Material <75$\mu$ | 61.26$^i$ | 3.06 | N/D |

$^i$Soluble Galactomannan.
$^{ii}$Total Galactomannan (Soluble + Insoluble).

EXAMPLE 4

This example shows the significant improvement and tablet hardness for a composition that uses the purified guar as compared to the commercially available material. Tablets were prepared using commercially available material from Mure Corporation MM1/2 Lot. No. 02-0142 for the comparison with the commercially available guar. The method of Example 3 was used to purify the material. Tablet hardness was measured by preparing four tablets of each formulation on a Stokes Model B216 station rotary tablet press. Tablets were prepared using 200 mg of guar with a 7 millimeter diameter, round, flat punch. Hardness was measured by using a Vandercamp™ VK200 Tablet Hardness Tester. Material of various particle sizes was prepared for the various batches of tablets. The results are summarized in Table 6. It can be seen that there is a significant difference between the hardness of the purified material versus the hardness of the unpurified material. It can also be seen that the hardness is significantly more for tablets prepared from a material with a particle size of 125 microns or less and the difference is even more distinct using material of 75 microns or less.

TABLE 5

Tablet Description: 200 mg, 7 mm Diameter, Round, Flat, n = 4.
Formulation: 100% Purified Guar Gum -
Meer MMM1/2 Lot No. 020142.

| Relative Humidity | Particle Size | Hardness Purified (kp) | Hardness Unpurified (kp) |
| --- | --- | --- | --- |
| 56% | 250–180$\mu$ | 0.00 ± 0.00 | 3.00 ± 0.10 |
| 56% | 125–106$\mu$ | 3.08 ± 0.13 | 0.97 ± 0.21 |
| 56% | <75$\mu^i$ | 6.95 ± 0.26 | 0.00 ± 0.00 |
| 56% | ⅓ of Each | 3.53 ± 0.24 | N/D$^{ii}$ |
| 75% | 150–180$\mu$ | 2.00 ± 0.22 | N/D |
| 75% | 125–106$\mu$ | 6.00 ± 0.34 | N/D |
| 75% | <75$\mu^i$ | 9.40 ± 1.10 | N/D |
| 75% | ⅓ of Each | 5.38 ± 0.22 | N/D |

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

The subject matter claimed is:

1. A process for increasing the hardness rating of a pharmaceutical tablet that is to contain guar gum, which process comprises
   mixing a composition consisting essentially of a purified galactomannan-based hydrocolloid with an active agent and optionally a pharmaceutically-acceptable excipient, and forming the pharmaceutical tablet by using a tablet press, wherein the purified galactomannan-based hydrocolloid exhibits
   about 50% to about 90% by weight anhydromannose residues and about 10% to about 50% by weight anhydrogalactose residues;
   less than about 1.0% by weight of protein material;
   less than about 3.0% by weight other non-aqueous impurities; and
   about 5% to about 15.0% by weight water.

2. The process of claim 1 wherein the protein material is less than 0.5% by weight and non-aqueous impurities are less than 2.0% by weight.

3. The process of claim 1 wherein the particle size of the hydrocolloid is less than 150 microns in diameter.

4. The process of claim 3 wherein the particle size is less than 125 microns.

5. The process of claim 4 wherein the particle size is less than 75 microns.

6. The process of claim 5 wherein the galactomannan hydrocolloid is derived from *Cyamopsis tetragonolobus*.

7. The process of claim 1 wherein the active agent is a corticosteroid.

8. The process of claim 7 wherein the corticosteroid is dexamethasone, budesnoide, fluticasone, predisolone, prednisone or hydrocortisone.

* * * * *